(12) United States Patent
Gros et al.

(10) Patent No.: US 10,716,809 B2
(45) Date of Patent: Jul. 21, 2020

(54) METHODS OF PRODUCING ENRICHED POPULATIONS OF TUMOR REACTIVE T CELLS FROM PERIPHERAL BLOOD

(71) Applicant: The United States of America, as represented by the Secretary, Department of Health and Human Services, Bethesda, MD (US)

(72) Inventors: Alena Gros, Barcelona (ES); Steven A. Rosenberg, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 94 days.

(21) Appl. No.: 15/813,398

(22) Filed: Nov. 15, 2017

(65) Prior Publication Data
US 2018/0133253 A1    May 17, 2018

Related U.S. Application Data

(62) Division of application No. 14/771,593, filed as application No. PCT/US2013/038813 on Apr. 30, 2013, now Pat. No. 9,844,569.

(60) Provisional application No. 61/771,251, filed on Mar. 1, 2013.

(51) Int. Cl.
*A61K 35/17* (2015.01)
*C12N 5/0783* (2010.01)
*G01N 33/50* (2006.01)
*G01N 33/569* (2006.01)

(52) U.S. Cl.
CPC .......... *A61K 35/17* (2013.01); *C12N 5/0636* (2013.01); *G01N 33/5005* (2013.01); *G01N 33/5094* (2013.01); *G01N 33/56972* (2013.01)

(58) Field of Classification Search
CPC .. A61K 35/17; C12N 5/0636; G01N 33/5094; G01N 33/56972; G01N 33/5005
USPC ........................................................ 424/93.7
See application file for complete search history.

(56) References Cited

U.S. PATENT DOCUMENTS

| 6,406,699 | B1 | 6/2002 | Wood |
| 7,977,095 | B2 | 7/2011 | Bonyhadi et al. |
| 8,034,334 | B2 | 10/2011 | Dudley et al. |
| 2004/0177394 | A1 | 9/2004 | Latif |
| 2008/0131415 | A1 | 6/2008 | Riddell et al. |
| 2012/0244133 | A1 | 9/2012 | Rosenberg et al. |
| 2013/0309213 | A1 | 11/2013 | Manjili et al. |
| 2019/0083539 | A1 | 3/2019 | Wardell et al. |

FOREIGN PATENT DOCUMENTS

| CN | 101625361 A | 1/2010 |
| CN | 104371974 A | 2/2015 |
| CN | 105754990 A | 7/2016 |
| CN | 106177931 A | 12/2016 |
| CN | 106957905 A | 7/2017 |
| CN | 108254557 A | 7/2018 |
| DE | 10392933 B4 | 4/2007 |
| JP | H09-505982 A | 6/1997 |
| JP | 2003-521936 A | 7/2003 |
| JP | 2011-510653 A | 4/2011 |
| JP | 2014-020930 A | 2/2014 |
| JP | 2018-082702 A | 5/2018 |
| MX | 2018012758 A | 1/2019 |
| RU | 2662916 C1 | 7/2018 |
| WO | WO 95/07995 A2 | 3/1995 |
| WO | WO 2001/059073 | 8/2001 |
| WO | WO 2007/018198 | 2/2007 |
| WO | WO 2009/097119 | 8/2009 |
| WO | WO 2012/054792 | 4/2012 |
| WO | WO 2012/129201 A1 | 9/2012 |
| WO | WO 2019/004415 A1 | 1/2019 |

OTHER PUBLICATIONS

Ahmadzadeh et al., "Tumor antigen-specific CD8 T cells infiltrating the tumor express high levels of PD-1 and are functionally impaired," *Blood*, 114(8): 1537-44 (2009).
Arai et al., "Upregulation of TIM-3 and PD-1 on CD4+ and CD8+ T Cells Associated with Dysfunction of Cell-Mediated Immunity after Colorectal Cancer Operation," *Yonago Acta Medica*, 55: 1-9 (2012).
Baitsch et al., "Exhaustion of tumor-specific CD8+ T cells in metastases from melanoma patients," *J. Clin. Invest.*, 121(6): 2350-60 (2011).

(Continued)

*Primary Examiner* — Yan Xiao
(74) *Attorney, Agent, or Firm* — Leydig, Voit & Mayer

(57) ABSTRACT

Methods of obtaining a cell population enriched for tumor-reactive T cells, the method comprising: (a) obtaining a bulk population of peripheral blood mononuclear cells (PBMCs) from a sample of peripheral blood; (b) specifically selecting CD8+ T cells that also express PD-1 and/or TIM-3 from the bulk population; and (c) separating the cells selected in (b) from unselected cells to obtain a cell population enriched for tumor-reactive T cells are disclosed. Related methods of administering a cell population enriched for tumor-reactive T cells to a mammal, methods of obtaining a pharmaceutical composition comprising a cell population enriched for tumor-reactive T cells, and isolated or purified cell populations are also disclosed.

11 Claims, 2 Drawing Sheets

(56) References Cited

OTHER PUBLICATIONS

Baitsch et al., "Extended Co-Expression of Inhibitory Receptors by Human CD8 T-Cells Depending on Differentiation, Antigen-Specificity and Anatomical Localization," *PLoS One*, 7(2): e30852 1-10 (2012).

Baruah et al., "Decreased levels of Alternative Co-Stimulatory Receptors OX40 and 4-1BB Characterise T Cells from Head and Neck Cancer Patients," Immunobiology, 217: 669-675 (2012).

Byers, T., "What can randomized controlled trials tell us about nutrition and cancer prevention?" *CA Cancer J. Clin.*, 49(6):353-61 (1999).

Duraiswamy et al., "Phenotype, Function, and Gene Expression Profiles of Programmed Death-1 hi CD8 T Cells in Healthy Human Adults," *J. Immunol.*, 186: 4200-12 (2011).

Gros et al., "Enrichment of melanoma-reactive cells from the fresh tumor digest through selection of CD8$^+$ T cells expressing PD-1, LAG-3, TIM-3, and 4-1BB," abstract for American Society of Gene & Cell Therapy (ASGCT) (2012).

Gros et al., "Enrichment of melanoma-reactive cells from the fresh tumor digest through selection of CD8$^+$ T cells expressing PD-1, LAG-3, TIM-3, and 4-1BB," poster presented at ASGCT (2012).

Gros et al., "PD-1 identifies the patient-specific CD8$^+$ tumor-reactive repertoire infiltrating human tumors," J. Clin. Invest., 124(5): 2246-59 (2014).

Gros et al., "Prospective identification of neoantigen-specific lymphocytes in the peripheral blood of melanoma patients," Nature Med., 22(4): 433-438 (2016).

Gros et al., "Selection of PD-1, LAG-3, TIM-3 and 41BB Positive CD8 T Cells in the Fresh Tumor Digest Enriches for Melanoma-Reactive Cells," Journal of Immunotherapy, 35(9):722-723 (2012).

Gros et al., "Selection of PD-1, LAG-3, TIM-3, and 4-1BB Positive CD8 T Cells in the Fresh Tumor Digest Enriches for Melanoma-Reactive Cells," presented at the Society for Immunotherapy of Cancer (SITC) on Oct. 28, 2012.

Gros et al., "Selection of PD-1, LAG-3, TIM-3, and 4-1BB Positive CD8 T Cells in the Fresh Tumor Digest Enriches for Melanoma-Reactive Cells," presented at the Society for Immunotherapy of Cancer (SITC) on Nov. 1, 2012.

Inozume et al., "Selection of CD8+PD-1+ Lymphocytes in Fresh Human Melanomas Enriches for Tumor-reactive T Cells," *J. Immunother.*, 33(9): 956-64 (2010).

International Searching Authority, International Search Report in International Application No. PCT/US2013/038813, dated Dec. 9, 2013.

International Searching Authority, Written Opinion in International Application No. PCT/US2013/038813, dated Dec. 9, 2013.

Jin et al., "Cooperation of Tim-3 and PD-1 in CD8 T-cell exhaustion during chronic viral infection," *PNAS*, 107(33): 14733-38 (2010).

Prieto et al., "Enrichment of CD8+ Cells from Melanoma Tumor-infiltrating Lymphocyte Cultures Reveals Tumor Reactivity for Use in Adoptive Cell Therapy," *J. Immunother.*, 33(5): 547-556 (2010).

Riley et al., "Stimulation of tumor-reactive T lymphocytes using mixtures of synthetic peptides derived from tumor-associated antigens with diverse MHC binding affinities," *J. Immunol. Methods*, 276: 103-119 (2003).

Rosenberg et al., "Durable Complete Responses in Heavily Pretreated Patients with Metastatic Melanoma Using T-Cell Transfer," *Clin. Cancer Res.*, 17(13): 4550-57 (2011).

Sakuishi et al., "Targeting Tim-3 and PD-1 pathways to reverse T cell exhaustion and restore anti-tumor immunity," *J. Exp. Med.*, 207(10): 2187-2194 (2010).

Wang et al., "The Stoichiometric Production of IL-2 and IFN-γ mRNA Defines Memory T Cells That Can Self-Renew After Adoptive Transfer in Humans," *Sci. Transl. Med.*, 4(149):149ra120 (2012).

Allied Market Research, "Cancer Immunotherapy Market Size, Share and Industry Analysis | 2022," (May 2017) accessed at <alliedmarketresearch.com/cancer-immunotherapy-market> on Jun. 19, 2019.

Bethune et al., "Personalized T cell-mediated cancer immunotherapy: progress and challenges," *Curr. Opin. Biotechnol.*, 48: 142-152 (2017).

BIS Research, "Global Cancer Immunotherapy Market is Projected to Reach $170.70 Billion by 2028," (Feb. 2019) accessed at <prnewswire.com/news-releases/global-cancer-immunotherapy-market-is-projected-to-reach-170-70-billion-by-2028--300797745.html> on Jun. 19, 2019.

Bobisse et al., Neoantigen-based cancer immunotherapy, *Ann. Transl. Med.*, 4(14): 262 (2016).

Giraldo et al., "Tumor-Infiltrating and Peripheral Blood T-cell Immunophenotypes Predict Early Relapse in Localized Clear Cell Renal Cell Carcinoma," *Clin. Cancer Res.*, 23(15): 4416-4428 (2017).

Grand View Research, "Cancer Immunotherapy Market Size | Industry Analysis Report," (Feb. 2019) accessed at <grandviewresearch.com/industry-analysis/cancer-immunotherapy-market> on Jun. 19, 2019.

Gros et al., "Selection of circulating PD-1+ lymphocytes from cancer patients enriches for tumor-reactive and mutation-specific lymphocytes," *J. Immunother. Cancer*, 3(Suppl 2): O2 (2015).

Iovance Biotherapeutics, Inc., "Immunotherapy for Solid Tumors," accessed at <iovance.com/clinical/immunotherapy-for-solid-tumors/> on Jun. 19, 2019.

Kite Pharma Inc., "Pipeline | KITE-718 MAGE A3/A6 clinical trial," accessed at <kitepharma.com/our-research/pipeline/> on Jun. 19, 2019.

Klebanoff et al., "Central memory self/tumor-reactive CD8$^+$ T cells confer superior antitumor immunity compared with effector memory T cells," *PNAS*, 102(27): 9571-9576 (2005).

Loo et al., "Emerging biomarkers as predictors to anti-PD1/PD-L1 therapies in advanced melanoma," *Immunotherapy*, 8(7): 775-784 (2016).

Miltenyi Biotec GmbH, "CD8+ CD279+ T cell isolation from peripheral blood," accessed at <miltenyibiotec.com/DE-en/resources/macs-handbook/human-cells-and-organs/human-cell-types/cd8-t-cells-human.html> on Jun. 19, 2019.

Research and Markets, (Dec. 2017) Cancer Immunotherapy—Global Market Outlook (2017-2023) accessed at <researchandmarkets.com/reports/4449913/cancer-immunotherapy-global-market-outlook> on Jun. 19, 2019.

Sfanos et al., "Human Prostate-Infiltrating CD8$^+$ T Lymphocytes are Oligoclonal and PD-1$^+$," *Prostate*, 69(15): 1694-1703 (2009).

Shi et al., "PD-1 and PD-L1 upregulation promotes CD8$^+$ T-cell apoptosis and postoperative recurrence in hepatocellular carcinoma patients," *Int. J. Cancer*, 128: 887-896 (2011).

Stemcell Technologies Inc., "EasySep™ Human T Cell Isolation Kit," accessed at <stemcell.com/easysep-human-t-cell-isolation-kit.html> on Jun. 19, 2019.

Thommen et al., "A transcriptionally and functionally distinct PD-1$^+$ CD8$^+$ T cell pool with predictive potential in non-small cell lung cancer treated with PD-1 blockade," *Nat. Med.*, 24(7): 994-1004 (2018).

Wikipedia, "Adoptive Cell Transfer," accessed at <en.wikipedia.org/wiki/Adoptive_cell_transfer#Cancer> on Jun. 19, 2019.

Xu et al., "Circulating and tumor-infiltrating Tim-3 in patients with colorectal cancer," *Oncotarget*, 6(24): 20592-20603 (2015).

Yee et al., "Personalized Therapy: Tumor Antigen Discovery for Adoptive Cellular Therapy," *Cancer J.*, 23(2): 144-148 (2017).

Zhang et al., "Breast Cancer Neoantigens Can Induce CD8$^+$ T-Cell Responses and Antitumor Immunity," *Cancer Immunol. Res.*, 5(7): 516-523 (2017).

Zhou et al., "Coexpression of Tim-3 and PD-1 identifies a CD8$^+$ T-cell exhaustion phenotype in mice with disseminated acute myelogenous leukemia," *Blood*, 117(17): 4501-4510 (2011).

Baumgaertner et al., "Ex vivo Detectable Human CD8 T-Cell Responses to Cancer-Testis Antigens," *Cancer Res.*, 66(4): 1912-1916 (2006).

Speiser et al., "Rapid and strong human CD8+ T cell responses to vaccination with peptide, IFA, and CpG oligodeoxynucleotide 7909," *J. Clin. Invest.*, 115(3): 739-746 (2005).

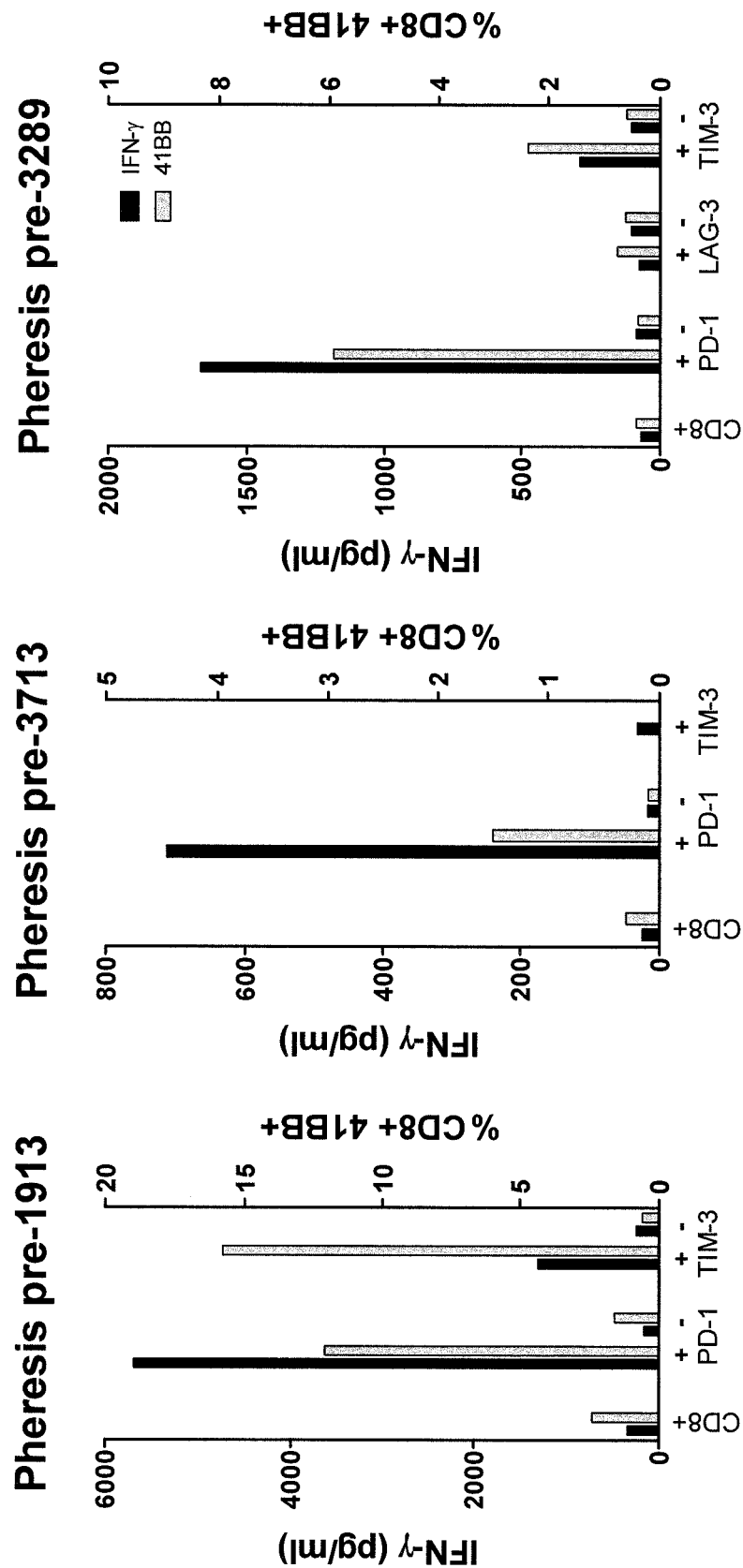

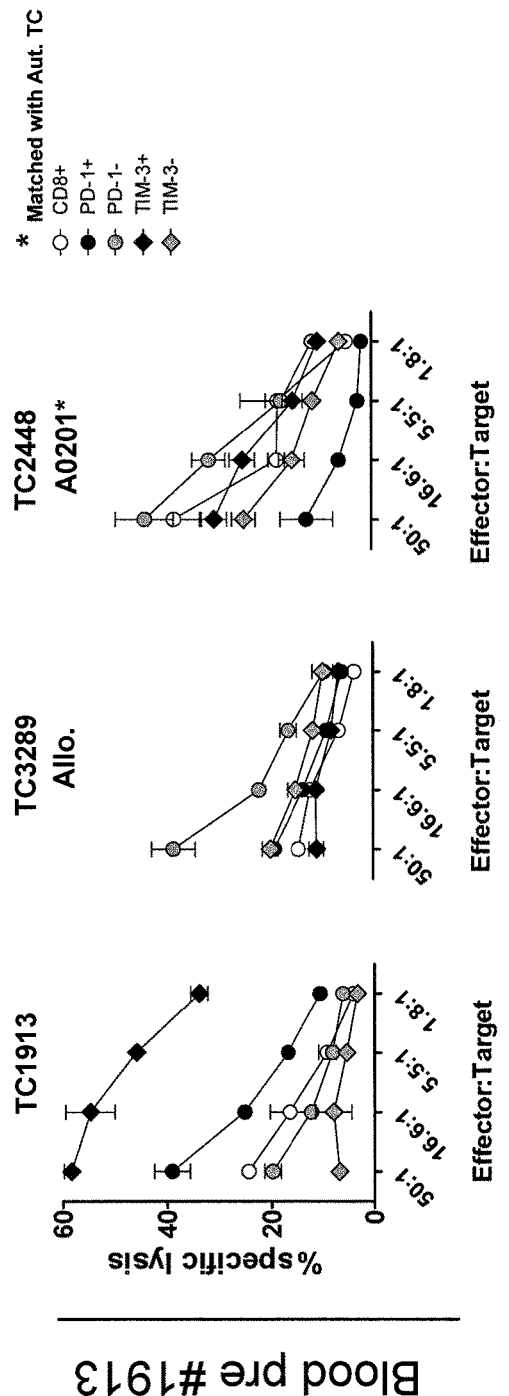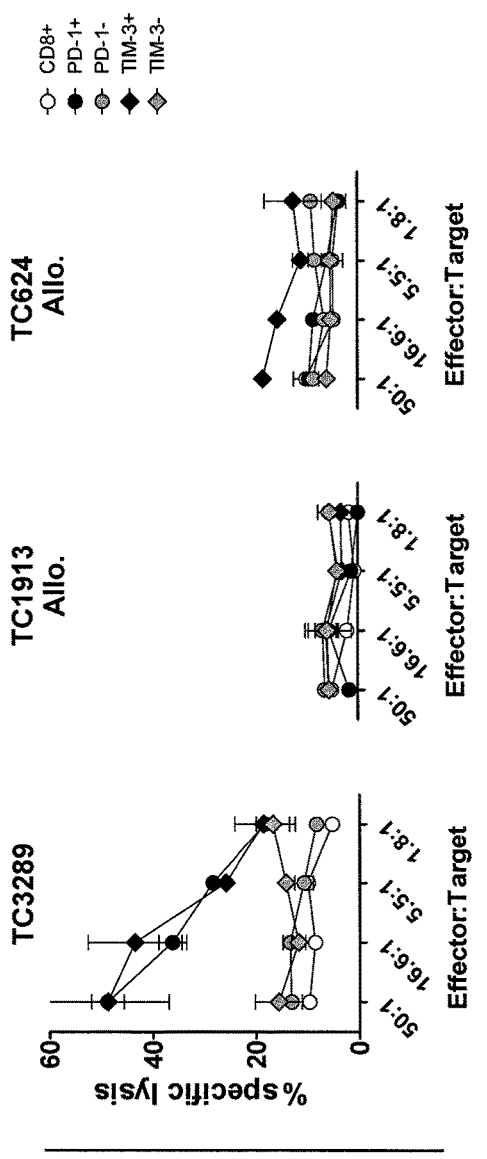

__

METHODS OF PRODUCING ENRICHED POPULATIONS OF TUMOR REACTIVE T CELLS FROM PERIPHERAL BLOOD

CROSS-REFERENCE TO RELATED APPLICATION APPLICATIONS

This patent application is a divisional of U.S. application Ser. No. 14/771,593, filed Aug. 31, 2015, which is a U.S. National Phase of International Patent Application No. PCT/US2013/038813, filed Apr. 30, 2013, which claims the benefit of U.S. Provisional Patent Application No. 61/771,251, filed Mar. 1, 2013, each of which is incorporated by reference in its entirety herein.

STATEMENT REGARDING FEDERALLY SPONSORED RESEARCH AND DEVELOPMENT

This invention was made with Government support under project number ZIABC010984 by the National Institutes of Health, National Cancer Institute. The Government has certain rights in the invention.

BACKGROUND OF THE INVENTION

Adoptive cell therapy (ACT) using tumor reactive T cells can produce positive clinical responses in some cancer patients. Nevertheless, several obstacles to the successful use of ACT for the treatment of cancer and other diseases remain. For example, T cells isolated from peripheral blood may not exhibit sufficient tumor-specific reactivity. Accordingly, there is a need for improved methods of obtaining a population of tumor-reactive T cells from peripheral blood.

BRIEF SUMMARY OF THE INVENTION

An embodiment of the invention provides a method of obtaining a cell population enriched for tumor-reactive T cells, the method comprising: (a) obtaining a bulk population of peripheral blood mononuclear cells (PBMCs) from a sample of peripheral blood; (b) specifically selecting $CD8^+$ T cells that also express PD-1 and/or TIM-3 from the bulk population; and (c) separating the cells selected in (b) from unselected cells to obtain a cell population enriched for tumor-reactive T cells.

Another embodiment of the invention provides a method of administering a cell population enriched for tumor-reactive T cells to a mammal, the method comprising: (a) obtaining a bulk population of PBMCs from a sample of peripheral blood; (b) specifically selecting $CD8^+$ T cells that also express PD-1 and/or TIM-3 from the bulk population; (c) separating the cells selected in (b) from unselected cells to obtain a cell population enriched for tumor-reactive T cells; and (d) administering the cell population enriched for tumor-reactive T cells to the mammal.

Still another embodiment of the invention provides a method of obtaining a pharmaceutical composition comprising a cell population enriched for tumor-reactive T cells, the method comprising: (a) obtaining a bulk population of PBMCs from a sample of peripheral blood; (b) specifically selecting $CD8^+$ T cells that also express PD-1 and/or TIM-3 from the bulk population; (c) separating the cells selected in (b) from unselected cells to obtain a cell population enriched for tumor-reactive T cells; and (d) combining the cell population enriched for tumor-reactive T cells with a pharmaceutically acceptable carrier to obtain a pharmaceutical composition comprising a cell population enriched for tumor-reactive T cells.

Additional embodiments of the invention provide related populations of cells and methods of treating or preventing cancer.

BRIEF DESCRIPTION OF THE SEVERAL VIEWS OF THE DRAWINGS

FIGS. 1A-1B are graphs showing interferon (IFN)-gamma secretion (pg/ml) (black bars) and percentage of $CD8^+$ cells expressing 4-1BB (grey bars) by cells that were isolated from the peripheral blood of melanoma patient 1913 (A) or melanoma patient 3713 (B) and which were sorted for expression of CD8, PD-1, or TIM-3 or lack of expression of PD-1 or TIM-3 by fluorescence-activated cell sorting (FACS) and expanded in vitro, upon co-culture against the autologous tumor cell line.

FIG. 1C is a graph showing IFN-gamma secretion (pg/ml) (black bars) and percentage of $CD8^+$ cells expressing 4-1 BB (grey bars) by cells that were isolated from the peripheral blood of melanoma patient 3289 and which were sorted for expression of CD8, PD-1, LAG-3, or TIM-3 or lack of expression of PD-1 or TIM-3 by FACS, upon co-culture against the autologous tumor.

FIGS. 2A-2C are graphs showing percent specific lysis of target autologous tumor cell line TC1913 (A), allogeneic (Allo.) tumor cell line TC3289 (B), or HLA-A0201-matched tumor cell line TC2448 (C) by effector cells isolated from the peripheral blood of patient 1913, sorted for expression as follows: $CD8^+$ (open circles), $PD-1^+$ (black circles), $PD-1^-$ (grey circles), $TIM-3^+$ (black diamonds), or $TIM-3^-$ (grey diamonds), and expanded in vitro.

FIGS. 2D-2F are graphs showing percent specific lysis of target autologous tumor cell line TC3289 (D), allogeneic tumor cell line TC1913 (E), or allogeneic tumor cell line TC624 (F) by effector cells isolated from the peripheral blood of patient 3289 (D-F) and sorted for expression as follows: $CD8^+$ (open circles), $PD-1^+$ (black circles), $PD-1^-$ (grey circles), $TIM-3^+$ (black diamonds), or $TIM-3^-$ (grey diamonds). Target cell lysis after in vitro expansion is shown.

DETAILED DESCRIPTION OF THE INVENTION

It has been discovered that selecting $CD8^+$ cells that also express programmed cell death protein 1 (PD-1; CD279) and/or T-cell immunoglobulin and mucin domain 3 (TIM-3) biomarkers enriches for tumor-reactive T cells present in peripheral blood. Selecting the $CD8^+$ cells that also express PD-1 and/or TIM-3 advantageously enriches for greater numbers of tumor-reactive T cells as compared to $CD8^+$ cells that do not express these markers.

In this regard, an embodiment of the invention provides a method of obtaining a cell population enriched for tumor-reactive T cells, the method comprising: (a) obtaining a bulk population of peripheral blood mononuclear cells (PBMCs) from a sample of peripheral blood; (b) specifically selecting $CD8^+$ T cells that also express PD-1 and/or TIM-3 from the bulk population; and (c) separating the cells selected in (b) from unselected cells to obtain a cell population enriched for tumor-reactive T cells. The inventive methods advantageously make it possible to shorten the time of in vitro culture and to select for tumor-reactive T cells without having to screen for autologous tumor recognition.

The method may comprise obtaining a bulk population of PBMCs from a sample of peripheral blood by any suitable method known in the art. Suitable methods of obtaining a bulk population of PBMCs may include, but are not limited to, a blood draw and/or a leukapheresis. The bulk population of PBMCs obtained from a tumor sample may comprise T cells, including tumor-reactive T cells.

The peripheral blood may be obtained from any mammal. Unless stated otherwise, as used herein, the term "mammal" refers to any mammal including, but not limited to, mammals of the order Logomorpha, such as rabbits; the order Carnivora, including Felines (cats) and Canines (dogs); the order Artiodactyla, including Bovines (cows) and Swines (pigs); or of the order Perssodactyla, including Equines (horses). It is preferred that the mammals are non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

The method may comprise specifically selecting $CD8^+$ T cells that also express PD-1 and/or TIM-3 from the bulk population. In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. For example, the specific selection of CD3, CD8, TIM-3, or PD-1 may be carried out using anti-CD3, anti-CD8, anti-TIM-3, or anti-PD-1 antibodies, respectively. Preferably, the antibody is chosen such that it specifically recognizes and binds to the particular biomarker being selected. The antibody or antibodies may be conjugated to a bead (e.g., a magnetic bead) or to a fluorochrome. Preferably, the flow cytometry is fluorescence-activated cell sorting (FACS).

In an embodiment of the invention, specifically selecting may comprise specifically selecting $CD8^+$ T cells that are positive for expression of any one of TIM-3, PD-1, or both TIM-3 and PD-1. In this regard, specifically selecting may comprise specifically selecting T cells that are single positive for expression of TIM-3 or PD-1 or double positive for simultaneous co-expression of TIM-3 and PD-1. In an embodiment of the invention, the method comprises specifically selecting $CD8^+$ T cells that express TIM-3 from the bulk population. In still another embodiment of the invention, the method comprises specifically selecting $CD8^+$ T cells that express PD-1 from the bulk population. Still another embodiment of the invention comprises specifically selecting $CD8^+$ T cells that are (i) $TIM-3^+/PD-1^+$, (ii) $TIM-3^-/PD-1^+$, or (iii) $TIM-3^+/PD-1^-$ from the bulk population. In another embodiment of the invention, any of the methods described herein may further comprise selecting cells that also express $CD3^+$.

In an embodiment of the invention, specifically selecting may comprise specifically selecting combinations of $CD8^+$ cells expressing any of the markers described herein. In this regard, the method may produce a cell population that is enriched for tumor-reactive cells that comprises a mixture of cells expressing any two of the biomarkers described herein. In an embodiment of the invention, specifically selecting comprises specifically selecting a combination of $PD-1^+$ cells and $TIM-3^+$ cells. In another embodiment of the invention, any of the methods described herein may further comprise selecting cells that also express $CD8^+$ and/or $CD3^+$.

The method may comprise separating the selected cells from unselected cells to obtain a cell population enriched for tumor-reactive T cells. In this regard, the selected cells may be physically separated from the unselected cells. The selected cells may be separated from unselected cells by any suitable method such as, for example, sorting. Separating the selected cells from the unselected cells preferably produces a cell population that is enriched for tumor-reactive T cells.

The cell populations obtained by the inventive methods are advantageously enriched for tumor-reactive T cells. In this regard, the cell populations obtained by the inventive methods may comprise a higher proportion of tumor reactive T cells as compared to cell populations that have not been obtained by sorting for expression of TIM-3 and/or PD-1.

In an embodiment of the invention, the method comprises obtaining the cell population enriched for tumor-reactive T cells without screening for autologous tumor recognition. In this regard, the inventive methods advantageously provide a cell population that is enriched for cells that have tumor reactivity without having to screen the cells for autologous tumor recognition.

In an embodiment of the invention, the method does not comprise non-specifically stimulating the bulk population of T cells prior to specifically selecting the cells. In this regard, the inventive methods advantageously provide a cell population that is enriched for tumor reactive T cells without stimulating the bulk population of T cells nonspecifically (e.g., with anti-4-1BB antibodies, anti-CD3 antibodies, and/or anti-CD28 antibodies).

In an embodiment of the invention, the method further comprises expanding the numbers of T cells in the enriched cell population obtained by the inventive methods in vitro. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in U.S. Pat. No. 8,034,334 and U.S. Patent Application Publication No. 2012/0244133, each of which is incorporated herein by reference.

In an embodiment of the invention, the method further comprises culturing the enriched cell population obtained by the inventive methods in the presence of any one or more of TWS119, interleukin (IL-21), IL-12, IL-15, IL-7, transforming growth factor (TGF) beta, and AKT inhibitor (AKTi). Without being bound to a particular theory, it is believed that culturing the enriched cell population in the presence of TWS119, IL-21, and/or IL-12 may, advantageously, enhance the anti-tumor reactivity of the enriched cell population by preventing or retarding the differentiation of the enriched cell population.

In an embodiment of the invention, the method further comprises transducing or transfecting the cells of the enriched population obtained by any of the inventive methods described herein with a nucleotide sequence encoding any one or more of IL-12, IL-7, IL-15, IL-2, IL-21, mir155, and anti-PD-1 siRNA.

In an embodiment of the invention, the method further comprises stimulating the enriched cell population obtained by the inventive methods with a cancer antigen and/or with autologous tumor cells. Stimulating the enriched cell population with a cancer antigen and/or with autologous tumor cells may be carried out by any suitable method. For example, stimulating the enriched cell population may be carried out by physically contacting the enriched cell population with a cancer antigen and/or with autologous tumor cells. Without being bound to a particular theory, it is believed that stimulating the enriched cell population with a cancer antigen and/or with autologous tumor cells may, advantageously, enhance the anti-tumor reactivity of the enriched cell population.

The term "cancer antigen" as used herein refers to any molecule (e.g., protein, peptide, lipid, carbohydrate, etc.) solely or predominantly expressed or over-expressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells. Exemplary cancer antigens may include any one or more of gp100, MART-1, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, NY-ESO-1, vascular endothelial growth factor receptor-2 (VEGFR-2), HER-2, mesothelin, and epidermal growth factor receptor variant III (EGFR III).

The inventive methods advantageously produce cell populations enriched for tumor-reactive T cells. The T cells may be tumor-reactive such that they specifically recognize, lyse, and/or and kill tumor cells. In this regard, an embodiment of the invention provides an isolated or purified cell population enriched for tumor-reactive T cells obtained by any of the inventive methods described herein. In an embodiment, the isolated or purified cell population comprises (a) $CD8^+/TIM-3^+/PD-1^+$ T cells, (b) $CD8^+/TIM-3^-/PD-1^+$ T cells, and (c) $CD8^+/TIM-3^+/PD-1^-$ T cells, wherein the cell population is enriched for tumor-reactive T cells. In another embodiment of the invention, the isolated or purified cell population comprises (a) $CD8^+/TIM-3^+/PD-1^+$ T cells, (b) $CD8^+/TIM-3^-/PD-1^+$ T cells, or (c) $CD8^+/TIM-3^+/PD-1^-$ T cells. In another embodiment of the invention, any of the cell populations described herein may also be $CD3^+$.

In an embodiment of the invention, the isolated or purified cell population comprises a mixture of cells expressing any of the biomarkers described herein. For example, the isolated or purified cell population may comprise a combination of $PD-1^+$ cells and $TIM-3^+$ cells. In another embodiment of the invention, any of the cell populations described herein may also be $CD8^+$ and/or $CD3^+$.

The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, 90% or can be 100%.

Another embodiment of the invention provides a method of administering a cell population enriched for tumor-reactive T cells to a mammal, the method comprising: (a) obtaining a bulk population of PBMCs from a sample of peripheral blood; (b) specifically selecting $CD8^+$ T cells that also express PD-1 and/or TIM-3 from the bulk population; (c) separating the cells selected in (b) from unselected cells to obtain a cell population enriched for tumor-reactive T cells; and (d) administering the cell population enriched for tumor-reactive T cells to the mammal. Obtaining a bulk population of PBMCs from a sample of peripheral blood, specifically selecting $CD8^+$ T cells that also express PD-1 and/or TIM-3 from the bulk population, and separating the selected cells from unselected cells to obtain a cell population enriched for tumor-reactive T cells may be carried out as described herein with respect to other aspects of the invention.

The method may further comprise administering the cell population enriched for tumor-reactive T cells to the mammal. The cell population enriched for tumor-reactive T cells may be administered in any suitable manner. Preferably, the cell population enriched for tumor-reactive T cells is administered by injection, e.g., intravenously.

The inventive cell population enriched for tumor-reactive T cells can be included in a composition, such as a pharmaceutical composition. In this regard, the invention provides a pharmaceutical composition comprising any of the cell populations described herein and a pharmaceutically acceptable carrier.

Another embodiment of the invention provides a method of obtaining a pharmaceutical composition comprising a cell population enriched for tumor-reactive T cells, the method comprising: (a) obtaining a bulk population of PBMCs from a sample of peripheral blood; (b) specifically selecting $CD8^+$ T cells that also express PD-1 and/or TIM-3 from the bulk population; (c) separating the cells selected in (b) from unselected cells to obtain a cell population enriched for tumor-reactive T cells; and (d) combining the cell population enriched for tumor-reactive T cells with a pharmaceutically acceptable carrier to obtain a pharmaceutical composition comprising a cell population enriched for tumor-reactive T cells. Obtaining a bulk population of PBMCs from a sample of peripheral blood, specifically selecting $CD8^+$ T cells that also express PD-1 and/or TIM-3 from the bulk population, and separating the selected cells from unselected cells to obtain a cell population enriched for tumor-reactive T cells may be carried out as described herein with respect to other aspects of the invention.

The method may comprise combining the cell population enriched for tumor-reactive T cells with a pharmaceutically acceptable carrier to obtain a pharmaceutical composition comprising a cell population enriched for tumor-reactive T cells. Preferably, the carrier is a pharmaceutically acceptable carrier. With respect to pharmaceutical compositions, the carrier can be any of those conventionally used for the administration of cells. Such pharmaceutically acceptable carriers are well-known to those skilled in the art and are readily available to the public. It is preferred that the pharmaceutically acceptable carrier be one which has no detrimental side effects or toxicity under the conditions of use. A suitable pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

For purposes of the invention, the dose, e.g., number of cells in the inventive cell population enriched for tumor-reactive T cells, administered should be sufficient to effect, e.g., a therapeutic or prophylactic response, in the mammal over a reasonable time frame. For example, the number of cells should be sufficient to bind to a cancer antigen, or detect, treat or prevent cancer in a period of from about 2 hours or longer, e.g., 12 to 24 or more hours, from the time of administration. In certain embodiments, the time period could be even longer. The number of cells will be determined by, e.g., the efficacy of the particular cells and the condition of the mammal (e.g., human), as well as the body weight of the mammal (e.g., human) to be treated.

Many assays for determining an administered number of cells from the inventive cell population enriched for tumor-reactive T cells are known in the art. For purposes of the invention, an assay, which comprises comparing the extent to which target cells are lysed or one or more cytokines such as, e.g., IFN-γ and IL-2 are secreted upon administration of a given number of such cells to a mammal, among a set of mammals of which is each given a different number of the cells, could be used to determine a starting number to be administered to a mammal. The extent to which target cells are lysed, or cytokines such as, e.g., IFN-γ and IL-2 are secreted, upon administration of a certain number of cells, can be assayed by methods known in the art. Secretion of cytokines such as, e.g., IL-2, may also provide an indication of the quality (e.g., phenotype and/or effectiveness) of a cell preparation.

The number of the cells from the inventive cell population enriched for tumor-reactive T cells also will be determined by the existence, nature and extent of any adverse side effects that might accompany the administration of a particular cell population. Typically, the attending physician will decide the number of the cells with which to treat each individual patient, taking into consideration a variety of factors, such as age, body weight, general health, diet, sex, route of administration, and the severity of the condition being treated. By way of example and not intending to limit the invention, the number of cells can be about $10 \times 10^6$ to about $10 \times 10^{11}$ cells per infusion, about $10 \times 10^9$ cells to about $10 \times 10^{11}$ cells per infusion, or $10 \times 10^7$ to about $10 \times 10^9$ cells per infusion. The cell populations obtained by the inventive methods may, advantageously, make it possible to effectively treat or prevent cancer.

It is contemplated that the cell populations obtained by the inventive methods can be used in methods of treating or preventing cancer. In this regard, the invention provides a method of treating or preventing cancer in a mammal, comprising administering to the mammal the pharmaceutical compositions or cell populations obtained by any of the inventive methods described herein in an amount effective to treat or prevent cancer in the mammal. Another embodiment of the invention provides a method of treating or preventing cancer in a mammal, comprising administering a cell population enriched for tumor-reactive T cells to a mammal by any of the inventive methods described herein in an amount effective to treat or prevent cancer in the mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount or any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

For purposes of the inventive methods, wherein populations of cells are administered, the cells can be cells that are allogeneic or autologous to the mammal. Preferably, the cells are autologous to the mammal.

An embodiment of the invention further comprises lymphodepleting the mammal prior to administering any of the enriched cell populations obtained by any of the inventive methods described herein. Examples of lymphodepletion include, but may not be limited to, nonmyeloablative lymphodepleting chemotherapy, myeloablative lymphodepleting chemotherapy, total body irradiation, etc.

With respect to the inventive methods, the cancer can be any cancer, including any of sarcomas (e.g., synovial sarcoma, osteogenic sarcoma, leiomyosarcoma uteri, and alveolar rhabdomyosarcoma), lymphomas (e.g., Hodgkin lymphoma and non-Hodgkin lymphoma), hepatocellular carcinoma, glioma, head-neck cancer, acute lymphocytic cancer, acute myeloid leukemia, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer (e.g., colon carcinoma), esophageal cancer, cervical cancer, gastrointestinal cancer (e.g., gastrointestinal carcinoid tumor), hypopharynx cancer, larynx cancer, liver cancer, lung cancer, malignant mesothelioma, melanoma, multiple myeloma, nasopharynx cancer, ovarian cancer, pancreatic cancer, peritoneum, omentum, and mesentery cancer, pharynx cancer, prostate cancer, rectal cancer, renal cancer, small intestine cancer, soft tissue cancer, stomach cancer, testicular cancer, thyroid cancer, ureter cancer, and urinary bladder cancer.

The following examples further illustrate the invention but, of course, should not be construed as in any way limiting its scope.

Example 1

This example demonstrates the in vitro autologous tumor recognition of T cells isolated from the peripheral blood of melanoma patients according to expression of PD-1, TIM-3, or LAG-3 after expanding the numbers of cells in vitro.

4-1BB up-regulation is an indicator of TCR stimulation. It has been observed that after the numbers of cells are expanded and in the absence of TCR stimulation, 4-1BB expression is lost. It has also been observed that after the numbers of cells are expanded and the cells are co-cultured with the autologous tumor cell line, T cells that had previously lost 4-1BB expression and which are stimulated by the cell line will re-express 4-1BB. Accordingly, 4-1BB expression is measured 24 hours after co-culture with autologous tumor as a marker of TCR stimulation against the autologous tumor cell line.

Cells obtained from the peripheral blood of each of three melanoma patients (1913, 3713, and 3289) by apheresis were rested over night without cytokines and stained. The cells from patients 1913 and 3713 were sorted into the following CD3$^+$ populations using anti-CD3, anti-CD8, anti-PD-1, and TIM-3 antibodies: CD8$^+$, CD8$^+$/PD-1$^+$, CD8/TIM-3', CD8$^+$/PD-1$^-$, or CD8$^+$/TIM-3$^-$ by fluorescence-activated cell sorting (FACS). The cells from patient 3289 were sorted into the following CD3$^+$ populations using anti-CD3, anti-CD8, anti-PD-1, TIM-3, and LAG-3 antibodies: CD8$^+$, CD8$^+$/PD-1$^+$, CD8$^+$/LAG3$^+$, CD8$^+$/TIM-3$^+$, CD8$^+$/PD-1$^-$, CD8$^+$/LAG3$^-$, or CD8$^+$/TIM-3$^-$ by FACS. The numbers of cells were expanded in vitro for 14 days. On day 14, cells were washed and co-cultured with the corresponding autologous tumor cell lines (1×10$^5$ effectors: 1×10$^5$ target cells) and reactivity was assessed by quantifying IFN-gamma release and percentage of CD8$^+$ cells expressing 41BB 24 hours after co-culture. The results are shown in FIGS. 1A-1C and Tables 1-3. As shown in FIGS. 1A-1C and Tables 1-3, cells sorted according to expression of PD-1 or TIM-3 were enriched for tumor-reactive cells as compared to cells that were negative for PD-1 or TIM-3 expression, respectively.

TABLE 1

| | | T cells | TC 1913 Aut. | TC1913 $^+$ W6/32 | FrTu#1913 Aut. | FrTu#1913 $^+$ W6/32 | TC 624 CIITA Allo. A0201 | TC 624 CIITA $^+$ W6/32 | TC 624 CIITA $^+$ HLA-DR |
|---|---|---|---|---|---|---|---|---|---|
| T$_{eff}$ Pheresis Pre-1913 | CD8$^+$ | 13 (0.3) | 342 (2.4) | 7 (0.4) | 1290 (1.4) | 46 (0.5) | 3942 (3.4) | 33 (0.7) | 2684 (2.1) |
| | PD-1$^+$ | 52 (1.3) | 5693 (12.1) | 56 (4.6) | 2122 (14.1) | 89 (1.8) | 6890 (3.0) | 15 (0.9) | 5610 (2.3) |
| | PD-1– | 18 (0.2) | 163 (1.6) | 4 (0.5) | 252 (1.0) | 38 (0.4) | 2047 (2.5) | 6 (0.3) | 1794 (1.7) |
| | TIM-3$^+$ | 144 (3.0) | 1303 (15.8) | 15 (0.9) | 1150 (8.4) | 138 (1.2) | 1389 (1.3) | 10 (0.4) | 1346 (1.6) |
| | TIM-3$^-$ | 0 (0.1) | 244 (1.3) | 0 (0.6) | 430 (1.1) | 16 (0.3) | 1754 (2.1) | 1 (0.5) | 1169 (1.6) |

| | | | TC 2119 A0201 | TC2448 A0201 | TC1865 A0201 | TC1379 A11 | TC2301 Allo | OKT3 (0.1 µg/ml) |
|---|---|---|---|---|---|---|---|---|
| T$_{eff}$ Pheresis Pre-1913 | | CD8$^+$ | 3099 (0.7) | 935 (1.9) | 1723 (2.8) | 1301 (3.6) | 328 (1.1) | 67357 (88.4) |
| | | PD-1$^+$ | 933 (2.0) | 413 (1.1) | 174 (1.4) | 43 (0.8) | 240 (1.0) | 53874 (86.1) |
| | | PD-1– | 2457 (1.7) | 439 (2.0) | 528 (3.1) | 158 (2.9) | 202 (1.2) | 41469 (89.1) |
| | | TIM-3$^+$ | 785 (2.6) | 1124 (5.4) | 113 (1.9) | 50 (2.9) | 46 (0.7) | 69564 (92.2) |
| | | TIM-3$^-$ | 1427 (0.7) | 1215 (1.1) | 608 (3.1) | 370 (2.3) | 262 (1.1) | 52940 (92.9) |

In vitro expanded effector populations isolated from peripheral blood of Patient 1913 according to expression of the cell surface markers indicated were co-cultured against the autologous (Aut.) tumor cells line (TC1913) and allogeneic (Allo.) tumor cells lines. Reactivity by IFN gamma (pg/ml) is shown. Values in parenthesis are the percentage of CD3$^+$ CD8$^+$ cells that up-regulated CD137 (41BB) 24 hours (h) after co-culture. Tumor cell lines (TC) 624 CIITA, 2119, 2448, and 1865 share HLA A*0201 allele with TC1913, and TC 1379 shares A*11 with TC1913. TC2301 is an allogeneic control (mismatched for all HLA) used as a negative control.
Values >300 pg/ml and greater than twice the background are considered positive and are shown underlined and in bold.

TABLE 2

| | | T cells | TC3713 Aut. | TC3713 $^+$ W6/32 | TC624 CIITA HLA-A0201 matched A*0201 | TC624 CIITA $^+$ W6/32 matched A*0201 | TC624 CIITA $^+$ HLA-DR matched A*0201 | TC2119 matched A*0201 | TC2119 $^+$ W6/32 | TC1379 Allo. | TC3460 Allo. | OKT3 (0.1 μ/ml) |
|---|---|---|---|---|---|---|---|---|---|---|---|---|
| Pheresis | CD3$^+$ CD8$^+$ | 0 (0) | 25 (0.3) | 0 (0) | 149 (0.6) | 0 (0.1) | 102 (0.2) | 634 (1.2) | 0 (0.2) | 50 (0.7) | 95 (0.1) | 24946 (71.9) |
| | PD-1$^+$ | 0 (0.3) | 713 (1.5) | 0 (0.7) | 68 (0.7) | 0 (0.2) | 53 (0.3) | 186 (0.9) | 0 (0.1) | 40 (1.2) | 186 (0.6) | 24044 (69.4) |
| | PD-1− | 0 (0) | 17 (0.1) | 0 (0.1) | 93 (0.4) | 10 (0.2) | 104 (0.4) | 216 (0.9) | 0 (0.1) | 71 (0.7) | 42 (0.1) | 26901 (74.2) |
| | Tim-3$^+$ | 31 (0.2) | 32 (0) | 5 (0.3) | 247 (0.4) | 8 (0.2) | 198 (0.4) | 281 (0.4) | 11 (0.2) | 26 (0.4) | 14 (0.2) | 43218 (69.9) |

In vitro expanded effector populations isolated from peripheral blood of patient 3713 according to expression of the cell surface markers indicated were co-cultured against the autologous tumor cells line (TC3713) and allogeneic tumor cells lines. Reactivity by IFN gamma (pg/ml) is shown. Values in parenthesis are the percentage of CD3$^+$ CD8$^+$ cells that up-regulated CD137 (41BB) 24 h after co-culture. Tumor cell lines (TC) 624 CIITA and 2119 share HLA A*0201 allele with TC3713. TC 1379 and TC 3460 are allogeneic target cell lines (mismatched for all HLA) used as a negative control.
Values >300 pg/ml and greater than twice the background are considered positive and are shown underlined and in bold.

TABLE 3

| | | T cells | $^+$ TC3289 Aut. | $^+$ TC3289 $^+$ W6/32 | $^+$ TC3289 (IFN-γ treatment) | $^+$ TC1379 Allo | $^+$TC526 Allo | $^+$ TC526 $^+$ W6/32 | $^+$ CD4$^+$ CD25− Aut. normal target | OKT3 (0.1 μ/ml) |
|---|---|---|---|---|---|---|---|---|---|---|
| Pheresis | CD3$^+$ CD8$^+$ | 120 (0.5) | 69 (0.4) | 44 (0.2) | 128 (0.5) | 37 (0.3) | 121 (0.6) | 34 (0.2) | 103 (0.8) | 93232 (87.8) |
| | PD-1$^+$ | 47 (0.6) | 1849 (5.9) | 1013 (1.8) | 969 (3.5) | 0 (0.5) | 109 (0.8) | 0 (0.1) | 35 (2.3) | 59617 (90.9) |
| | PD-1− | 157 (0.5) | 85 (0.4) | 58 (0.1) | 125 (0.5) | 66 (0.4) | 164 (1.0) | 46 (0.2) | 124 (1.0) | 70009 (88.9) |
| | LAG-3$^+$ | 158 (0.8) | 76 (0.8) | 50 (0.3) | 101 (0.5) | 29 (0.4) | 71 (1.0) | 30 (0.3) | 124 (1.5) | 84514 (78.4) |
| | LAG-3− | 234 (1.0) | 102 (0.6) | 57 (0.3) | 132 (0.5) | 56 (0.5) | 95 (0.8) | 43 (0.2) | 144 (1.2) | 70004 (88.5) |
| | Tim-3$^+$ | 434 (2.2) | 289 (2.4) | 118 (0.4) | 450 (1.6) | 128 (1.1) | 448 (1.4) | 111 (0.4) | 247 (2.2) | 46674 (87.8) |
| | Tim-3− | 196 (0.6) | 103 (0.6) | 77 (0.2) | 147 (0.4) | 105 (0.6) | 113 (0.8) | 63 (0.2) | 142 (1.2) | 95104 (88.0) |

In vitro expanded effector populations isolated from the peripheral blood of Patient 3289 according to expression of the cell surface markers indicated were co-cultured against the autologous tumor cells line (3289) and allogeneic tumor cells lines. Reactivity by IFN gamma (pg/ml) is shown. Values in parenthesis are the percentage of CD3$^+$ CD8$^+$ cells that up-regulated CD137 (41BB) 24 h after co-culture. Tumor cell lines (TC) 1379 and TC526 are allogeneic cell lines (missmatched for all HLA) and autolgous CD4$^+$ CD25$^-$ cells isolated from peripheral blood used as a negative control.
Values >300 pg/ml and greater than twice the background are considered positive and are shown underlined and in bold.

Example 2

This example demonstrates the in vitro autologous tumor recognition of T cells isolated from the peripheral blood of melanoma patients and sorted according to expression of PD-1 or TIM-3 after expanding the numbers of cells in vitro.

Cells were obtained from the peripheral blood of patient 1913 or patient 3289 and were sorted according to expression of PD-1 or TIM-3 by FACS as described in Example 1. The numbers of sorted cells were expanded for 14 days in vitro. On day 15, target tumor cell lines (autologous and allogeneic) were labeled with $^{51}$Cr and co-cultured for 4 hours with the sorted populations of cells (effector cells) at the ratios shown in FIGS. 2A-2F. $^{51}$Cr release was determined in triplicate by γ-counting and the percentage of specific lysis was calculated using the following formula: [(experimental counts per minute (cpm)−spontaneous cpm)/(maximal cpm−spontaneous cpm)]×100. The results are shown in FIGS. 2A-2F. As shown in FIGS. 2A-2F, cells obtained from peripheral blood and sorted for PD-1$^+$ or TIM-3$^+$ expression are capable of lysing the autologous tumor cell line.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of obtaining a cell population enriched for tumor-reactive T cells, the method comprising:
   (a) obtaining a bulk population of peripheral blood mononuclear cells (PBMCs) from a sample of peripheral blood;
   (b) specifically selecting CD8$^+$ T cells that also express PD-1 and/or TIM-3 from the bulk population; and
   (c) separating the cells selected in (b) from unselected cells to obtain a cell population enriched for tumor-reactive T cells.

2. A method of obtaining a pharmaceutical composition comprising a cell population enriched for tumor-reactive T cells, the method comprising:
   (a) obtaining a bulk population of peripheral blood mononuclear cells (PBMCs) from a sample of peripheral blood;
   (b) specifically selecting CD8$^+$ T cells that also express PD-1 and/or TIM-3 from the bulk population;
   (c) separating the cells selected in (b) from unselected cells to obtain a cell population enriched for tumor-reactive T cells; and
   (d) combining the cell population enriched for tumor-reactive T cells with a pharmaceutically acceptable carrier to obtain a pharmaceutical composition comprising a cell population enriched for tumor-reactive T cells.

3. The method of claim 1, wherein (b) comprises specifically selecting CD8$^+$ T cells that express TIM-3 from the bulk population.

4. The method of claim 1, wherein (b) comprises specifically selecting CD8$^+$ T cells that express PD-1 from the bulk population.

5. The method of claim 1, wherein (b) comprises specifically selecting CD8$^+$ T cells that are (i) TIM-3$^+$/PD-1$^+$, (ii) TIM-3$^-$/PD-1$^+$, or (iii) TIM-3$^+$/PD-1$^-$ from the bulk population.

6. The method of claim 1, wherein the cell population enriched for tumor-reactive T cells is obtained without screening for autologous tumor recognition.

7. The method of claim 1, wherein the bulk population of T cells is not non-specifically stimulated prior to (b).

8. The method of claim 1, further comprising expanding the numbers of T cells in the enriched cell population obtained in (c).

9. The method of claim 1, further comprising culturing the enriched cell population obtained in (c) in the presence of any one or more of TWS119, interleukin (IL-21), IL-12, IL-15, IL-7, transforming growth factor (TGF) beta, and AKT inhibitor (AKTi).

10. The method of claim 1, further comprising stimulating the enriched cell population obtained in (c) with a tumor antigen and/or with autologous tumor T cells.

11. The method of claim 1, further comprising transducing or transfecting the cells of the enriched population obtained in (c) with a nucleotide sequence encoding any one or more of IL-12, IL-7, IL-15, IL-2, IL-21, mir155, and anti-PD-1 siRNA.

* * * * *